(12) United States Patent
Mortari et al.

(10) Patent No.: US 7,749,757 B1
(45) Date of Patent: Jul. 6, 2010

(54) STABILIZING SOLUTION FOR CELLS AND TISSUES

(75) Inventors: Frank Mortari, Woodbury, MN (US); Paige M Johnson, Saint Louis Park, MN (US); Alan M Johnson, New Brighton, MN (US)

(73) Assignee: Research & Diagnostic Systems, Inc., Minneapolis, MN (US)

(*) Notice: Subject to any disclaimer, the term of this patent is extended or adjusted under 35 U.S.C. 154(b) by 401 days.

(21) Appl. No.: 11/839,172

(22) Filed: Aug. 15, 2007

Related U.S. Application Data

(62) Division of application No. 10/407,499, filed on Apr. 4, 2003, now Pat. No. 7,267,980.

(51) Int. Cl.
*A01N 1/00* (2006.01)
*C12N 5/00* (2006.01)
*A61K 38/00* (2006.01)

(52) U.S. Cl. .................... 435/325; 435/1.1; 435/2; 435/375

(58) Field of Classification Search ................ 435/325, 435/1.1, 2, 375
See application file for complete search history.

(56) References Cited

U.S. PATENT DOCUMENTS

| | | | |
|---|---|---|---|
| 4,698,312 A | 10/1987 | Wong et al. |
| 4,933,293 A | 6/1990 | Kuroda et al. |
| 5,262,327 A | 11/1993 | Ryan |
| 5,270,208 A | 12/1993 | Ryan |
| 5,312,744 A | 5/1994 | Shibata |
| 5,422,277 A | 6/1995 | Connelly et al. |
| 5,459,073 A | 10/1995 | Ryan |
| 5,478,722 A | 12/1995 | Caldwell |
| 5,672,474 A | 9/1997 | Ryan |
| 5,677,145 A | 10/1997 | Ryan |
| 5,731,205 A | 3/1998 | Ryan |
| 5,981,282 A | 11/1999 | Ryan |
| 6,072,086 A | 6/2000 | James et al. |
| 6,197,540 B1 | 3/2001 | Granger et al. |
| 6,319,683 B1 | 11/2001 | James et al. |
| 6,406,915 B2 | 6/2002 | Ryan et al. |

OTHER PUBLICATIONS

Caldwell, C.W., Cytometry Jul. 1, 1994; 16(3):243-9.
Muramoto, L.M., et al., Am. J. Clin. Pathol. Nov. 1987; 88(5):589-95.
Boyles, J., et al., J. Cell Biol Oct. 1985; 101(4):1463-72.
McLean, I.W. et al., J. Histochem Cytochem vol. 22, No. 12, pp. 1077-1083 (1974).
Hixson, D.C., et al., J. Histochem Cytochem vol. 29, No. 4, pp. 561-566 (1981).
Luther, et al., J. Histochem Cytochem vol. 37, No. 1, pp. 75-82 (1989).
Rogers, S., Imaging Technology Group, Technical Report 99-066, Cell Biological Applications of Fluorescence Microscopy (www.itg.uiuc.edu/publications/techreports/99-066/fixation.htm), 2005.
Lal, R.B., et al., J. STD AIDS Jan. 1990; 1(1):38-45 (Abstract only).
Holgate, C.S., et al., J. Pathol. Aug. 1986:149(4) 293-300 (Abstract only).
Moench, T.R., et al., J. Virol Methods Jun. 1985;11(2) 119-30 (Abstract only).
Gendelman, H.E., et al., J. Immunol Methods Dec. 16, 1983;65(1-2):137-45 (Abstract only).
Hyde, J. C., et al., Histochemistry Feb. 26, 1976; 46(3):261-8 (Abstract only).
Hancock, W.W., Am J. Clin Pathol Dec. 1982;78(6):825-31 (Abstract only).
Mizuno, Y., et al., Natl Inst Anim Health Q (Tokyo) 1982 Spring;22(1):34-5 (Abstract only).

*Primary Examiner*—Ruth A Davis
(74) *Attorney, Agent, or Firm*—Fredrikson & Byron, P.A.

(57) ABSTRACT

Methods and compositions for stabilizing tissues, cells, and cell components such that desired antigenic sites, light scatter properties and cellular morphology are preserved for a useful period of time. The stabilizing solution includes glycine, lysine and formaldehyde.

21 Claims, 2 Drawing Sheets

| STABILIZING AGENTS | LIGHT SCATTER PROPERTIES | CD3/CD4 ANTIBODY STAINING |
|---|---|---|
| FRESH WHOLE BLOOD | <br>1A | <br>1B |
| FORMALDEHYDE + LYSINE | <br>1C | <br>1D |
| FORMALDEHYDE + GLYCINE | <br>1E | <br>1F |
| FORMALDEHYDE + LYSINE + GLYCINE | <br>1G | <br>1H |

2A

2B

2C

STABILIZING SOLUTION FOR CELLS AND TISSUES

CROSS-REFERENCE TO RELATED APPLICATION

This application is a divisional application of U.S. patent application Ser. No. 10/407,499, filed Apr. 4, 2003, and claims priority therefrom. U.S. patent application Ser. No. 10/407,499 is incorporated by reference herein.

FIELD OF THE INVENTION

The present invention generally relates to formulations containing compositions useful in the stabilization and fixation of cells and tissues and more particularly to a composition that preserves antigenic sites, cellular morphology, and light scatter properties of cells for a useful period of time.

BACKGROUND OF THE INVENTION

Analysis of biological specimens is a vital and critical technique for both clinical and research applications. However, depending on the source material and processing methods, it is often impossible to analyze specimens immediately after procurement. Thus, various techniques for fixation and stabilization of biological specimens have been developed.

These methods all strive to maintain antigenic sites of interest while still providing for robust preservation of the biological source material. Of the many different types of techniques that have been described in the literature, most of these utilize various chemical compounds that preserve antigenic sites through chemical cross-linking Aldehydes are some of the most commonly used chemical fixatives. It has been shown in the literature that aldehyde-fixation occurs through a Schiff acid-base reaction resulting from the formation of covalent bonds between adjacent amine-containing groups. Formaldehyde is one of the most commonly used aldehydes for fixation. Formalin is a commercial preparation of formaldehyde in solution.

Despite the wide use of formaldehyde in fixation techniques, there are drawbacks to its use for some applications. Formaldehyde fixation actually occurs through two distinct kinetic phases. At neutral pH, it penetrates the cell, modifies primary amines such as lysine, thiols such as cysteine, as well as purine nucleic acid bases. At higher pH, the cross-linking process occurs more rapidly. However, over extended time, formaldehyde continues to react with methylol derivatives. These secondary reactions can result in the eventual degradation of antigenic sites and the native light scatter properties of the cells may be modified. Thus, it may be necessary to remove the formaldehyde after the desired level of fixation has been achieved. The fixation time is generally an empirical measure that must be optimized depending on the type of specimen and antigenic determinants. This represents a significant drawback.

SUMMARY OF THE INVENTION

The present inventors have developed a novel and unique cell stabilization solution and method for use. The present invention comprises a solution having a sufficient amount of lysine, glycine and formaldehyde to stabilize cells and tissue while preserving antigenic sites, cellular morphology and desired light scatter properties of the cells. The success of any process to stabilize cells for flow cytometric analysis is best assessed with tests that address two key issues: 1) retention of cellular morphology over a defined period of time, and 2) retention of immunoreactivity of cells over a defined period of time. Typically, strong fixatives alter cellular volume and morphology to a point where instrumentation no longer recognizes the particle as a mammalian cell. Therefore retention of light scatter signature, normally used to initially identify mammalian cells of different lineages, needs to be maintained following any type cell fixation process. Secondly, the full identity of cells is most accurately assessed with the aid of antibodies. Since antibody reactivity is a key indicator of cell lineage, retention of immunoreactivity for a defined period of time is another indicator that the cell stabilization has been successful.

In an embodiment of the invention, lysine is present at a molar ratio between 0.1 to 0.5 moles of lysine per mole of formaldehyde, glycine is present at a molar ratio between 0.1 moles to 0.5 moles of glycine per mole of formaldehyde. In one aspect of the invention, the pH of the stabilizing solution of the invention ranges between 7.0 and 7.5.

In one embodiment of the invention, the stabilizing solution includes approximately 0.2 moles of lysine per mole of formaldehyde and approximately 0.3 moles of glycine per mole of formaldehyde. The pH of the stabilizing solution of the invention in this embodiment was 7.4.

Stabilized cells obtained using the stabilizing solution of the invention may be used in blood control products. The stabilized cells desirably exhibit good specific staining properties, that is, retention of specific binding determinants on the cell surface over a period of time, low non-specific staining properties and at least one light scatter property of the cells, existing prior to the stabilization process is preserved.

DETAILED DESCRIPTION OF THE INVENTION

Figure 1:
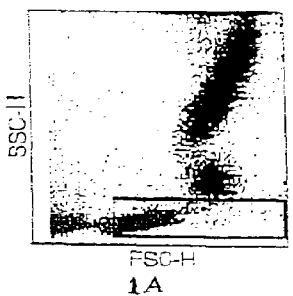
FIG. 1 shows flow cytometry results, light scatter and antibody staining properties, obtained using a stabilizing solution of the invention to stabilize human blood cells. The performance of the stabilized cells is compared to untreated fresh whole blood cells.
Figure 1:
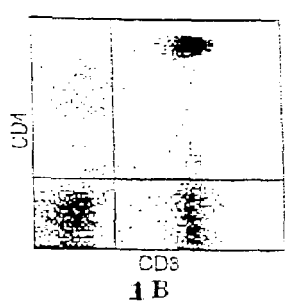
Figure 1:
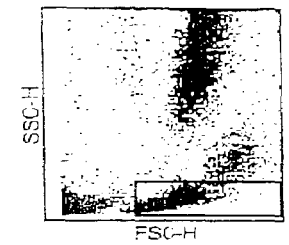
Figure 1:
Figure 1:
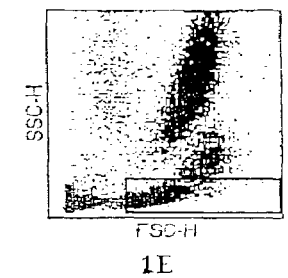
Figure 1:
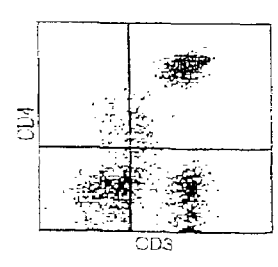
Figure 1:
Figure 1:
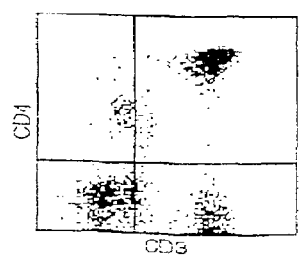

The present invention relates to a stabilizing solution that includes lysine, glycine and formaldehyde in cell compatible buffers or solvents. The solution is useful for, among other things, preserving and/or stabilizing cells and tissues for use as flow cytometry controls, the transport of cell or tissue samples for future flow cytometry analysis, for assays to determine characteristics of the preserved cells and tissues.

The term "fixed" as used herein refers to the practice of adding a chemical compound for preserving cell structure for analysis. Although a fixed cell remains physically stable for an extended period, some cellular antigens may not be optimally preserved, which in turn is detrimental to any testing activity (antibody mediated staining, separation, labeling, etc.) which normally requires antigen and cellular integrity.

The term "stabilized" is used herein to signify a cell treated with a solution of the invention that maintains antigen integrity, retention of cellular morphology, and light scatter properties, as measured by current instrumentation, in a reproducible manner over time. A stabilized cell can be successfully and reproducibly stained, separated, or labeled in an antigen-specific reaction. The further usefulness of the stabilization solution of this invention is in its ability to maintain the broadest reactivity of cells with a variety of well defined antibodies, this number being a minimum of, but not limited to, 43 different cluster designation (CD) markers as defined by the Council on Human Leucocyte Differentiation Antigens. See, *Proceedings of the Seventh International Workshop and Conference on Human Leucocyte Differentiation Antigens*, Oxford University Press, 2002, edited by David Mason et al.

References to a blood control describes a blend of stabilized cells from various tissues and lineages such that the final product has a defined composition and when tested by appropriate means yields results within a pre-assigned range for each of the parameters being monitored. Such controls are provided to measure the consistency and/or accuracy of diagnostic instruments and/or methods of analysis of patient samples. Thus, such controls are manufactured to provide expected values for the various blood components. These expected values are assigned by the control manufacturer. Such controls are preferably stable, so that they allow the user to establish whether the diagnostic instrument performs consistently and whether it reports the expected values. The control thus serves an important quality control function in clinical laboratories, offering assurance that the instruments and technicians are working properly and other variables are maintained in acceptable limits.

The amount of lysine, glycine and formaldehyde in the fixative of the invention is sufficient to stabilize cells for a particular application. Generally, the amounts of components in the stabilizing solution of the invention fall in the following ranges: for glycine the range is between about 0.05 to 0.5 grams per liter, and in one embodiment of the invention 0.3 grams per liter is used; for lysine the range is between 0.01 to 0.8 grams per liter and in one embodiment 0.6 grams per liter is used and for formaldehyde (37% w/v) the range is between about 0.2 to 2 milliliter per liter. In one aspect of the invention, the stabilizing solution will stabilize mammalian cells for at least 14 days and in one embodiment will stabilize the cells for a period of about 90 days following the stabilization step and separation of the cells from the stabilizing solution.

The stabilizing solution of the invention may also include any of the other components conventionally added to fixative or stabilizing preparations. These additional components may include mordants, buffers, cell penetration increasers, osmotically active substances and nuclear detail improvers. Examples of suitable materials that may be used to stabilize cells include: procaine hydrochloride, 1-hydroxypyridine-2-thione, acetamido iminodiacetic acid, chlorhexidene diacetate, paraformaldehyde, sodium sulfate, polyethylene glycol, and aniline and derivatives of aniline, and ammonium sulphate. Suitable buffers include phosphate buffered saline supplemented with antimicrobials such as penicillin, streptomycin, erythromycin, cycloheximide and serum proteins derived from human, bovine, mouse or rat origin.

Stabilized cells obtained using the stabilization solution of the invention may be used in various applications including use in a blood control product. The control product typically includes red blood cells (RBC), white blood cells (WBC) (or analogs thereof), including without limitation, lymphocytes, monocytes, neutrophils, eosinophils and basophils, and platelets (or analogs thereof), reticulocytes, suspended in a plasma-like fluid containing suitable preservatives. A number of suitable methodologies for the preparation of RBCs, WBCs, and platelets are well know by those skilled in the art. In addition, it is well known in the art to use various analogs that mimic the physical characteristics of the different human blood cell components, but that may be easier to produce, more cost-effective, or provide greater shelf life. The control product of the invention includes one or more of the cell types mentioned above that have been stabilized by suspending the cells in the stabilizing solution of the invention.

In one embodiment, glycine, lysine and formaldehyde are mixed with distilled water or other suitable solvent and may be used to stabilize cells from fresh blood. Typically, blood is drawn and used within 12 hours following the draw, although longer delays up to about 36 hours may be acceptable. If desired, specific cell types may be enriched or depleted. Alternatively, blood cell components such as enriched white blood cells, red blood cells or platelets may also be used. Cells may be used directly, or washed, with such agents as phosphate buffered saline, which may contain preservatives (such as sodium azide, 0.01%) or cell protectants (such as fetal bovine serum, 0.5%) to assist in the maintenance of cellular integrity during the processing steps.

The total cell count may be determined on a standard hematology analyzer and used to determine an optimal amount of required fixative. In one embodiment, concentrated WBCs are diluted in stabilizing solution to a range of between 25 to $250 \times 10^6$ cells/mL, and desirably, the WBCs will be diluted in fixative to $50 \times 10^6$ cells/mL. In one aspect of the invention, concentrated RBCs will be diluted in stabilizing solution to a range of between 0.5 to $10 \times 10^9$ cells/mL, and desirably, the RBCs will be diluted to $1.5 \times 10^9$ cells/mL.

In one embodiment, the cells are incubated in the stabilizing solution of the invention in a sealed container at room temperature for at least two days, typically from 3 to 6 days, and may be mixed by some means periodically. One mixing means useful in the method of the invention is the use a roller rotating at an appropriate speed, typically about 1-5 rev/min. Alternatively, the cells in stabilizing solution may be incubated at a temperature of 2-8° C. The length of the incubation period will vary depending on the cells or tissue being treated and the application for which the preserved cells will be used. After incubation, cells are harvested by centrifugation to remove the stabilizing solution, washed with phosphate buffered saline containing 0.01% sodium azide, or other suitable buffers, and, desirably, diluted with a buffer that aids in the preservation of the cellular integrity for extended periods of time. This buffer may contain proteins such as bovine albumin, sodium or potassium salts, antimicrobials and phosphates. Cells may be allowed to sit in this buffer for 0-30 days prior to concentrating and formulating them as a blood control that simulates fresh whole blood for flow cytometry analysis.

The stabilizing solution of the invention desirably preserves cellular morphology for a minimum of 30 days. Many fixative solutions currently in use have a propensity to shrink cells as a result of the dehydration process that is inherent in these fixation procedures. As a result the characteristic cellular morphology signature, as measured by light scattering properties used by most instruments to discriminate cells of different lineages, is altered.

The retention of antibody reactivity for at least about thirty days by the cells stabilized using the stabilizing solution of the invention is one indicator that the stabilizing solution has preserved antigenic sites on the cells in question. Antibody reactivity is routinely demonstrated through the use of antibodies directly conjugated to fluorescent dyes that impart fluorescence onto the cells they may interact with. Cellular fluorescence may then be monitored by flow cytometric analysis.

The stabilizing solution of the invention preserves antigenic sites of cells in their native confirmation that retains antibody reactivity and other specific binding pair reactivity. Conventional fixatives may alter protein structure on cells. This in turn changes the conformational structure of the protein and can thereby alter the epitope or receptor that particular antibodies or ligands are uniquely designed to recognize Preservation of antibody reactivity is an indicator that the molecular structure of the antigen has been substantially preserved and for many applications a stabilizing process that preserves such sites is very useful. "Specific binding pair" means any substance that selectively recognizes and interacts with a determinant on the surface or within a cell. Specific binding pairs include antigen-antibody, antigen-antibody fragment, receptor-hormone, receptor-ligand, agonist-antagonist, lectin-carbohydrate, nucleic acid (RNA or DNA) hybridizing sequences, Fc receptor or mouse IgG-protein A, avidin-biotin, streptavidin-biotin and virus-receptor interactions. Other determinant-specific binding pair combinations may be used with the method of this invention. The term "antibody" as used herein, includes immunoglobulins, monoclonal or polyclonal antibodies, immunoreactive immunoglobulin fragments, single chain antibodies and any other peptide with defined reactivities for specific cell molecules.

In another embodiment, the stabilizing solution of the invention may be used to stabilize cultured cells. In one application cells from a variety of tumors are harvested from tissue culture by centrifugation. Cells may be used directly, or washed with phosphate buffered saline or other similar solvents, which may contain preservatives, such as sodium azide, 0.1%, or cell protectants, such as fetal bovine serum, 0.5%. Concentrated cells are, in one embodiment, resuspended and diluted to $1$-$10 \times 10^6$ cells/mL, or other concentrations found appropriate, with the stabilizing solution containing formaldehyde, glycine and lysine in approximately a 5:1:1 molar ratio. The cells are desirably allowed to sit in fixative at temperatures of 2-8° C. for 2 to 6 days. After incubation, cells are harvested by centrifugation, typically at 2500 RPM for 10 minutes, to remove the stabilizing solution, washed with phosphate buffered saline with 0.1% sodium azide, or other suitable solvents, and diluted with a buffer that aids in the preservation of the cell integrity. This buffer may contain proteins such as bovine albumin, sodium or potassium salts, and antimicrobials such as cycloheximide. Cells may be allowed to sit in this buffer for up to 14 days prior to concentrating and formulating them as a control material. Cells may be immunophenotyped and analyzed by flow cytometry either unmodified, or blended with other stabilized cells to simulate pathological specimens.

In yet another embodiment, blood cell samples may be stabilized using the stabilizing solution of the invention for future analysis, for transport or for distribution to multiple laboratories (for example in a laboratory proficiency testing exercise). An optimized concentration of stabilizing solution would allow it to be added to the sample to be transported without concern of large dilution effects on the sample. The result is a sample that retains the original characteristics, numbers and proportions of cell populations but now has extended shelf life stability. An optimized formulation of the stabilizing solution for this specific purpose will have the formaldehyde, lysine and glycine concentrations increased 30-fold, to keep an approximate 5:1:1 molar ratio of the three key constituents. The stabilizing solution may be added to blood samples at varying volume ratios, from 5:1 to 15:1 ratio of whole blood to fixative (for example, 0.5-1.0 mL of fixative in a 7 mL blood tube). The blood sample may then be stored at temperatures 2-8° C. for a minimum of at least 7 days without impacting immunophenotypic analysis. The stabilization of these types of samples is ideally suited for those samples that require transport from the collection site to the center where flow cytometric analysis to determine the immunological composition of blood sample may be carried out. Antibody based analysis of hematological specimens is a useful technique in the identification of specific cell populations that may be either over or under represented. These anomalies are useful indicators of various pathologies; for example leukemia, lymphomas and myelomas are typically associated with elevated levels of selected cells normally expressing immature CD markers, while AIDS is typically characterized by reduced levels of $CD4^+$ lymphocytes.

In one embodiment of the invention, the stabilizing solution is used to stabilize samples that mimic pathological specimens. Having ready access to a variety of pathological specimens is an important aspect of the educational exercise conducted in clinical and research institutions. Various legal and medical restrictions normally prevent access to pathological specimens. Furthermore, in the early phases of an instructional exercise it may be prudent not to use potentially infectious specimens to better protect the staff. The current invention allows for the stabilization of normal specimens and following their modifications they could be used to simulate a pathological condition thereby making them useful test samples in a clinical setting. For example, HIV infected individuals normally present with very low absolute $CD4^+$ cell counts in their peripheral blood. The monitoring of $CD4^+$ cell counts has been adopted as a tool to both diagnose and monitor AIDS disease progression. Recognizing the infectious nature of blood derived from HIV infected individuals, the present invention allows one to mimic an HIV infected individual and use the resulting sample to test the proficiency of a laboratory to accurately enumerate $CD4^+$ cell counts.

The stabilizing solution of the invention is particularly useful in stabilizing specimens that contain elevated levels of rare cells. The stabilized rare cells may then be used for testing a lab's proficiency in the immunodetection of such cells. A cell type is considered a "rare cell type" when it represents less than about 10% of the cells in a biological sample. Usually, however, the rare cell will represent much fewer than 10% of the cells in a population. Typically the rare cell will represent fewer than about 1% of the cells in a population, often fewer than about 0.1%, frequently less than about 0.01%, and very often, as in the case of fetal cells in maternal circulation, fewer than about 0.0001% of the cell population from which it is derived (e.g., the population of cells in maternal whole blood). Cell populations containing rare cells of interest may be from a variety of biological sources including whole blood or blood fractions, bone marrow, cord blood, cerebral spinal fluid, saliva, bronchoaveolar lavage, continuously growing cell lines and tissue biopsies.

One example of use of the solution of the invention with rare cells is the detection of human $CD34^+$ cells commonly used in bone marrow transplantation. The need to accurately assess $CD34^+$ cells in transplant specimens arises from the fact that a transplant recipient requires a specific dose of $CD34^+$ cells per Kg of body weight, a desired dose ranges around $1 \times 10^5$ $CD34^+$ cells/Kg. Since these $CD34^+$ cells are very rare (normally found in peripheral blood at a frequency around 0.01% of total WBCs and found in relative abundance only in bone marrow and umbilical cord blood, having a specimen available for the training and proficiency testing purposes of lab staff can be difficult. The present invention circumvents these difficulties by allowing the stabilization of these rare cells with full retention of their morphological and immunophenotypic staining properties. In one embodiment of the current invention, $CD34^+$ cells enriched by mechanical means, usually magnetic separation or fluorescence activated cell sorting, are diluted in the stabilizing solution such that the cell concentration ranges between 1 and $10 \times 10^6$ cells/mL. Cells are left in the fixative for 3 to 6 days and then washed to remove excess fixative. The CD34$^+$ cells can now be admixed with stabilized normal human peripheral blood cells such that blood controls that contain varying concentrations of CD34$^+$ cells may be created. In one formulation, a blood control containing varying levels of CD34$^+$ (from 10-500 CD34$^+$ cells/uL) can offer any lab a procedure for determining their ability to accurately identify and enumerate rare cells.

The stabilizing procedure of the invention stabilizes CD34$^+$ rare cells while retaining key features of the cells, such as large lymphoid morphology with respect to light scatter, dim CD45 antibody staining and bright CD34 antibody staining, required for accurate identification of human CD34$^+$ cells.

Retention of the aforementioned cellular properties is one improvement of the stabilizing solutions of this invention. Other commonly used stabilizing solutions routinely make use of chemical entities that distort cellular morphology. Strong fixative solutions usually result in poor to no preservation of many cellular proteins used for antibody mediated identification of cell types and lineages. The current invention preserves cells with minimal disruption of their native features.

The stabilizing solution of the invention is also useful to stabilize cells for monoclonal antibody selection. The hybridoma technology first described by G. Kohler and C. Milstein relies on the ability to rapidly select the correct cell hybrid producing the appropriate antibody and to expand this cell in a selective media. One step in this process is the need to readily have access to large quantities of antigen at the time of the hybridoma screening step. For a simple antigen, such as soluble proteins, recombinant expression of these proteins will yield sufficient product to perform an ELISA type assay and select suitable antibody producing cells using an "antigen-down" approach where antigen is directly coated on tissue culture plastic. For complex antigens, such as those expressed on cell membranes, a useful screening tool are cells expressing high levels of the antigen of interest. However, having large quantities of exponentially growing cells at the appropriate time can be challenging.

The stabilizing solution of the current invention may be used to stabilize cells that have been induced to over-express the antigen of interest through gene transfection technology. Transfected cells may be incubated with the stabilizing solution for a period of 2-4 days. The fixed cells may now be exposed to the different antibodies present in the culture wells of an antibody producing hybridoma fusion collection, which could number anywhere from 1,000 to 10,000 culture wells. Since the test cells remain stable for at least 14 days, the investigator can now grow and stock pile sufficient quantities of the desired cells for the hybridoma screening exercise.

In a modified application for screening antibody-secreting hybridomas, the assay can include another cell type that serves as a negative staining control. These negative control cells are cells of the same genotypic and phenotypic origin as the transfected cells but have not been transfected with the gene of interest. These cells are commonly referred to as parental or wild-type cells. These control cells must first be fixed for 2-4 days with the fixative described in the invention. These cells are then mixed in equal proportions with stabilized transfected cells expressing the complex antigen of interest. Under these conditions, the correct antibody reactivity should stain and detect 50% of the cells. The remaining 50%, which represents the control cells, should not be stained and serve as an indicator of inappropriate antibody reactivity.

This exercise is rendered possible by the ability of the fixative described herein to retain protein folding conformations as close as possible to the native state of the cells. The utility of the current invention is in providing a time-saving tool for the isolation and identification of useful monoclonal antibodies to complex antigens from a large collection of antibodies.

Without being bound by theory, the inventors of the present invention hypothesize that the presence of lysine in the stabilizing solution of the invention, facilitates carbohydrate cross-linking while the formaldehyde potentiates amine cross-linking through Schiff acid-base reactions. The presence of glycine may serve to quench the deleterious secondary fixation effects of formaldehyde that could result in the degradation of antigenic sites. The chemical balance provided by the key formulation ingredients during the kinetics of the chemical reaction is paramount to achieving the desired cell stabilizing effects.

The invention will be further described with reference to the following non-limiting Examples. It will be apparent to those skilled in the art that many changes can be made in the embodiments described in the Examples without departing from the scope of the present invention. Thus the scope of the present invention should not be limited to the embodiments described in this application, but only by the embodiments described by the language of the claims and the equivalents of those embodiments.

Example 1

Stabilization of Fresh Blood

Human blood was collected and fractionated by aphoresis. Leucopacks enriched for WBCs were further concentrated by centrifugation, with removal of the bulk of RBCs, platelets and plasma. Cells were washed, with phosphate buffered saline, containing 0.1% azide.

The cells were incubated in a stabilizing solution which included 0.2 moles of lysine per mole of formaldehyde and 0.3 moles of glycine per mole of formaldehyde, pH 7.4, and other additives from the following commercial suppliers:

Materials:

Formaldehyde, 37% w/v (Sigma/Part # F-1635

Procaine Hydrochloride (Sigma/Part # P-9879)

ADA/N-(2-Acetamido)-2-Iminodiocetic Acid (Sigma/Part # A-9883)

Pyrithione/2-Mercaptopyridine-N-Oxide, sodium salt, 40% (Avocado/Part # A16922)

Sodium Hydroxide (Fluka/Part # 71691)

Sodium Sulfate (Sigma/Part #S-9627)

Sodium Chloride (Sigma/Part #S-9625)

Lysine (Sigma/Part #L-5626)

Glycine (Sigma/Part #G-7126)

The total cell count was determined on a standard hematology analyzer. Concentrated WBCs were diluted in stabilizing solution to a concentration of $50 \times 10^6$ cells/mL. Concentrated RBCs were diluted in stabilizing solution to a concentration of $1.5 \times 10^9$ cells/mL.

The cells were incubated in the stabilizing solution of the invention in a sealed container at room temperature for at least four days, and mixed using a roller rotating at a speed of about 5 rev/min. After incubation, cells were harvested by centrifugation to remove the stabilizing solution, washed with phosphate buffered saline containing 0.01% sodium azide, and diluted with a buffer containing phosphate buffered saline supplemented with 3% BSA, 3% sugars and antimicrobials.

The data shown in Table 1 shows that a blood control formulated from the above stabilized WBCs and RBCs can be used to accurately monitor various immunophenotypic parameters over a 71 day period. The data was derived using commercial reagents and flow cytometry instrumentation and software. Values were derived using an automated software program (SimulSet) from BD Bioscience. In Table 1, we provided as a reference the accepted range of cell subpopulations, as defined by CD markers, for a normal blood specimen. The similarity in recovered values between the stabilized blood control and the normal blood specimen was an indication of the success of the stabilization procedure.

TABLE 1

| Cell Population | Expected Values[1] % of total lymphocytes (range) | Stabilized Blood (13 days post stabilization) | Stabilized Blood (48 days post stabilization) | Stabilized Blood (71 days post stabilization) |
| --- | --- | --- | --- | --- |
| $CD3^+$ | 75 (59-85) | 72 | 72 | 70 |
| $CD3+/CD4^+$ | 43 (29-57) | 45 | 48 | 44 |
| $CD3+/CD8+$ | 25 (11-38) | 25 | 23 | 25 |
| $CD19^+$ | 13 (6.4-23) | 15 | 13 | 11 |
| $CD3-/CD16^+56^+$ | 14 (5.6-31) | 12 | 16 | 16 |

Example 2

Demonstration of Use of Stabilizing Solution to Obtain Stabilization of Human WBCs and RBCs Suitable for Flow Cytometric Analysis WBCs were collected by aphoresis and then stabilized by exposure to stabilizing solutions containing the following stabilizing formulations: 15 mM formaldehyde plus 3 mM lysine or 15 mM formaldehyde plus 4 mM glycine or 15 mM formaldehyde plus 3 mM lysine plus 4 mM glycine. Cells were stabilized for 4 days in the stabilizing solution and then blended with human RBCs also stabilized in the same manner. The final product was resupended in phosphate buffered saline supplemented with 3% BSA, 3% sugars and antimicrobials. These stabilized controls (FIGS. 1D, 1F, 1H) were processed for antibody staining for two CD markers, CD3-Fluorescein and CD4-Phycoerythrin, and RBCs lysis in parallel with a fresh whole blood sample (FIG. 1B) using commercial reagents obtained from BD Bioscience. These data clearly show that the formaldehyde, lysine and glycine mixture is critical for optimal cell stabilization. In the Figures we show light scatter 1A and antibody staining properties 1B of whole blood as collected by flow cytometry that can be used as reference data for comparison purposes. In FIGS. 1C & 1D we demonstrate the same flow cytometry analysis of cells stabilized with only formaldehyde and lysine. Note that there was retention of light scatter properties in this stabilized preparation but the antibody staining was compromised (as evidenced by the reduced staining intensity with the CD4 antibody which indicative of poor epitope preservation during the stabilization process). In FIGS. 1E & 1F where only formaldehyde and glycine were used to stabilize the cells, the antibody staining was found to be acceptable, however, the light scatter of these cells was compromised as evidenced by the poor resolution of the three cell populations, especially between the lymphocyte and monocyte cell clusters (compare the light scatter of these cells with those from fresh blood. Loss of light scatter is also indicative of poor preservation of cellular morphology during the stabilization process. In FIGS. 1G & 1H we see that WBCs and RBCs stabilized with formaldehyde plus lysine and glycine give improved light scatter and antibody staining results compared to fresh whole blood. This latter formulation of stabilizing agents yields cells with optimal properties desirable in a blood control preparation.

Example 3

Figure 2:
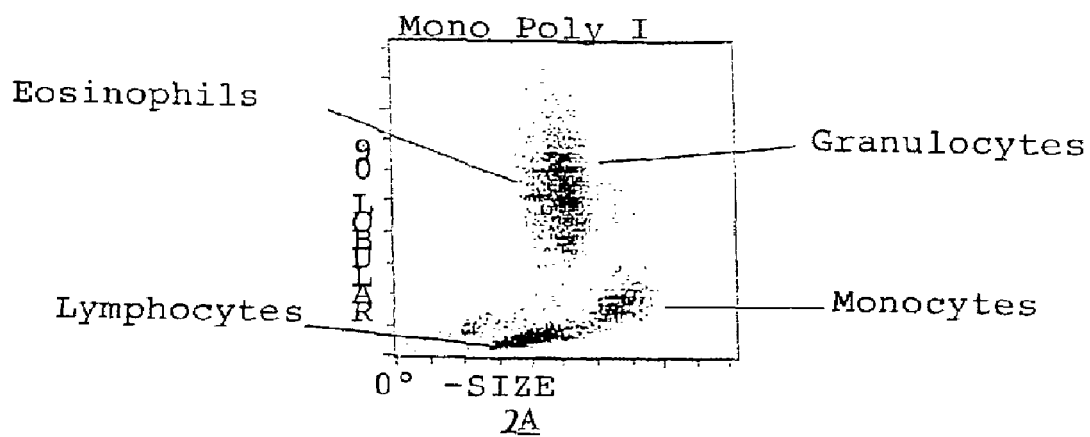
FIG. 2 shows the ability of the stabilizing solution of the invention to stabilize freshly collected blood specimens as assessed by analysis on a hematology analyzer. The stabilized blood specimen is compared to freshly drawn whole blood and an aged blood sample.
Figure 2:
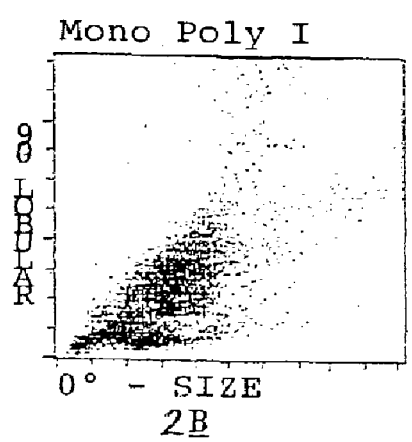
Figure 2:
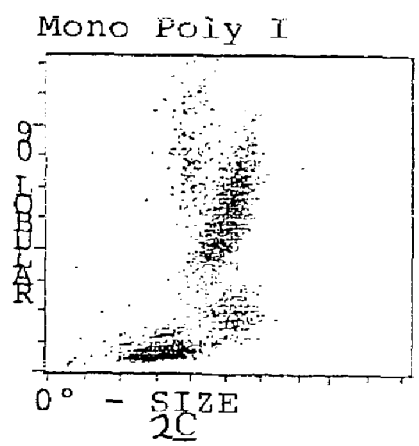

Demonstration of Use of Human Whole Blood Stabilized with the Stabilizing Solution on a Hematology Instrument for Differential WBCs Analysis In FIG. 2A we show a CellDyn-4000 hematology instrument analysis of a fresh whole blood sample. Note that four WBC populations are easily identified by this instrument on this display. In FIG. 2B we show the same instrument analysis on the same blood sample after it has aged for 14 days (without stabilization). Note that the instrument was unable to distinguish the same four WBC populations as above (compare FIG. 2B to FIG. 2A). FIG. 2C provides evidence that blood collected in an EDTA tube and stabilized with 0.5 mL of stabilizing solution containing 0.5 M formaldehyde plus 0.1 M lysine plus 0.1 M glycine stabilized the blood sample and allowed it to be processed accurately by the hematology analyzer. Note that whole blood cells stabilized as described in the invention retained the necessary properties to allow the instrument to accurately classify all four WBC populations (FIG. 2C).

Example 4

Stabilization of Cells Used to Simulate a Pathological Specimen

Human WBCs were collected by aphoresis and split into two pools of cells. One pool was mechanically depleted of the population of interest, in this example, $CD4^+$ T cells, using a cell separation column. Other separation devices known in the art may be used such as the use of magnetic particles coated with an appropriate monoclonal antibody. Following depletion of the targeted cells, the remaining cells were stabilized by the addition of the stabilizing solution (15 mM formaldehyde plus 3 mM lysine plus 3 mM glycine, pH 7.4) such that the cell concentration was between 25 and $250 \times 10^6$ cells/mL. The other pool of non-manipulated cells was also diluted in the fixative such that the cellular count was between 25 and $250 \times 10^6$ cells/mL. Both cell pools were left in fixative for 3 to 6 days. Once the cells were fully stabilized, stabilizing solution was removed and the cells resuspended in a phosphate buffered saline supplemented with 3% BSA, 3% sugars and antimicrobials. Since one cell pool is deficient of $CD4^+$ cells, while the other has a normal counterpart of $CD4^+$ cells, the two cell pools were admixed at a preferred ratio to arrive at a desired level of $CD4^+$ cells. In this example, a mixture containing 70% volume from the $CD4^+$ deficient cell pool and 30% from the $CD4^+$ replete cell pool was blended. This produced a stabilized blood control with a $CD4^+$ cell count that approximates the diagnostic cutoff level of the $CD4^+$ cell counts in those individuals suffering from AIDS, that is approximately 200 $CD4^+$ cells/gL.

Samples formulated in this manner were stable for periods greater than 30 days from the date of preparation and retained their absolute CD4⁺ cell count for that period. Such samples offer great value in a clinical setting where they can be utilized as a regular monitor of a lab's ability to accurately determine the absolute CD4⁺ cell count. An important aspect of the invention is that the above-described CD4 cell analysis may be conducted without risk of exposing laboratory personnel to highly infectious agents, such as HIV.

What is claimed is:

1. A method of fixing mammalian cells comprising suspending said cells in a fixative solution wherein said fixative solution comprises lysine, glycine and formaldehyde, the amount of each component being sufficient to fix the mammalian cells.

2. The method of claim 1 further comprising the step of subsequently separating the cells from the fixative solution.

3. The method of claim 2 further comprising suspending the cells separated from the fixative solution in a protein containing buffer solution.

4. The method of claim 1 wherein the cells are white blood cells.

5. The method of claim 1 wherein the cells are red blood cells.

6. The method of claim 1 wherein the cells are platelets.

7. The method of claim 1 wherein the cells are cultured tumor cells.

8. The method of claim 1 wherein the cells have at least one antigenic determinant in common with a cell representing less than 10% of the cells in a biological sample of whole blood, a blood fraction, bone marrow, cord blood, cerebral spinal fluid, saliva, bronchoalveolar lavage, a continuously growing cell line or a tissue biopsy and wherein the antigenic determinant is preserved by the lysine, glycine and formaldehyde solution.

9. The method of claim 1 wherein the solution further comprises one or more additional components selected from the group consisting of: mordants, buffers, cell penetration increasers, osmotically active substances and nuclear detail improvers.

10. The method of claim 9 wherein the additional component comprises procaine hydrochloride, 1-hydroxypyridine-2-thione, acetamido iminodiacetic acid, chlorhexidene diacetate, paraformaldehyde, sodium sulfate, polyethylene glycol, aniline, derivatives of aniline, or ammonium sulphate.

11. The method of claim 9 wherein the additional component is a buffer comprising phosphate buffered saline supplemented with an antimicrobial or serum protein derived from human, bovine, mouse or rat origin.

12. The method of claim 1 comprising:
formaldehyde in the range of about 0.007% to about 0.07% (w/v);
lysine in the range of about 0.001% to about 0.08% by (w/v) of the solution; and
glycine in the range of about 0.005% to about 0.05% (w/v) of the solution.

13. The method of claim 12 wherein the cells retain antibody reactivity.

14. The method of claim 13 wherein the antibodies are cluster designation marker antibodies.

15. The method of claim 1 wherein the solution fixes the cells to preserve the reactivity of the cells with at least two different cluster designation markers.

16. The method of claim 1 wherein fixing the mammalian cells comprises preserving cellular structure, at least one antigenic site and at least one light scatter property of the cells.

17. A method for fixing cells for use in formulating a flow cytometry control, comprising:
suspending said cells in a fixative solution, wherein said fixative solution comprises lysine, glycine and formaldehyde and subsequently separating the cells from the solution.

18. The method of claim 17, further comprising suspending the separated cells in a buffer comprising protein in the range of 1-5%.

19. The method of claim 18, wherein the buffer includes an antimicrobial.

20. The method of claim 19, wherein the antimicrobial is cycloheximide.

21. The method of claim 17 wherein fixing the cells comprises preserving cellular structure, at least one antigenic site, and at least one light scatter property of the cells.

* * * * *